United States Patent
Kim

(10) Patent No.: US 12,064,529 B2
(45) Date of Patent: Aug. 20, 2024

(54) PARTIALLY CURED CONTACT LENS-TYPE AMNIOTIC MEMBRANE DRESSING AND METHOD OF MANUFACTURING SAME

(71) Applicants: Kyungpook National University Industry-Academic Cooperation Foundation, Daegu (KR); Kyungpook National University Hospital, Daegu (KR)

(72) Inventor: Hong Kyun Kim, Daegu (KR)

(73) Assignees: Kyungpook National University Industry-Academic Cooperation Foundation, Daegu (KR); Kyungpook National University Hospital, Daegu (KR)

(*) Notice: Subject to any disclaimer, the term of this patent is extended or adjusted under 35 U.S.C. 154(b) by 795 days.

(21) Appl. No.: 17/056,352

(22) PCT Filed: Jan. 10, 2019

(86) PCT No.: PCT/KR2019/000394
§ 371 (c)(1),
(2) Date: Nov. 17, 2020

(87) PCT Pub. No.: WO2019/221360
PCT Pub. Date: Nov. 21, 2019

(65) Prior Publication Data
US 2021/0205496 A1    Jul. 8, 2021

(30) Foreign Application Priority Data

May 17, 2018    (KR) ........................ 10-2018-0056479

(51) Int. Cl.
*A61L 27/36*    (2006.01)

(52) U.S. Cl.
CPC ........ *A61L 27/3604* (2013.01); *A61L 27/3666* (2013.01); *A61L 27/3687* (2013.01); *A61L 27/3691* (2013.01); *A61L 2300/414* (2013.01); *A61L 2430/16* (2013.01)

(58) Field of Classification Search
CPC ............. A61L 27/3604; A61L 27/3666; A61L 27/3687; A61L 27/3691; A61L 2430/16; A61L 2300/414
See application file for complete search history.

(56) References Cited

U.S. PATENT DOCUMENTS

| | | |
|---|---|---|
| 8,957,032 B2 | 2/2015 | Alkan et al. |
| 2006/0134170 A1 | 6/2006 | Griffith et al. |
| 2011/0189301 A1 | 8/2011 | Yang |
| 2015/0277147 A1 | 10/2015 | Kim |

FOREIGN PATENT DOCUMENTS

| | | |
|---|---|---|
| KR | 20070053217 A | 5/2007 |
| KR | 10-2011-0005838 A | 1/2011 |
| KR | 10-2011-0090242 A | 8/2011 |
| KR | 10-1187423 B1 | 10/2012 |
| KR | 10-201400561126 | 5/2014 |

OTHER PUBLICATIONS

Yang et al., 2011 (US 2011/018930 A1, equivalent of KR10-2011-0090242).*
Schorgl et al., 2010 (US 20100228335 A1, Sep. 9, 2010).*
Tanaka et al., 2012 (Journal of Tissue Engineering and Regenerative Medicine, p. 1-7).*
International Search Report for corresponding PCT Application No. PCT/KR2019/000394 mailed Apr. 17, 2019.

* cited by examiner

*Primary Examiner* — Shin Lin Chen

(74) *Attorney, Agent, or Firm* — Wood, Phillips, Katz, Clark & Mortimer

(57) ABSTRACT

The present invention relates to a contact lens-type dressing manufactured by using a partially cured amniotic membrane dressing and a method of manufacturing same. The method of manufacturing a partially cured contact lens-type amniotic membrane dressing, and the partially cured contact lens-type amniotic membrane dressing of the present invention have a simple manufacturing method, can produce a contact lens-type amniotic membrane without foreign matter, have excellent biocompatibility, have excellent lens compatibility such as transparency and tensile strength compared to a fully cured contact lens-type amniotic membrane dressing, and also have excellent wound healing effects, and therefore, can be effectively used for the treatment of eye diseases such as corneal damage.

4 Claims, 10 Drawing Sheets

[Fig. 1]
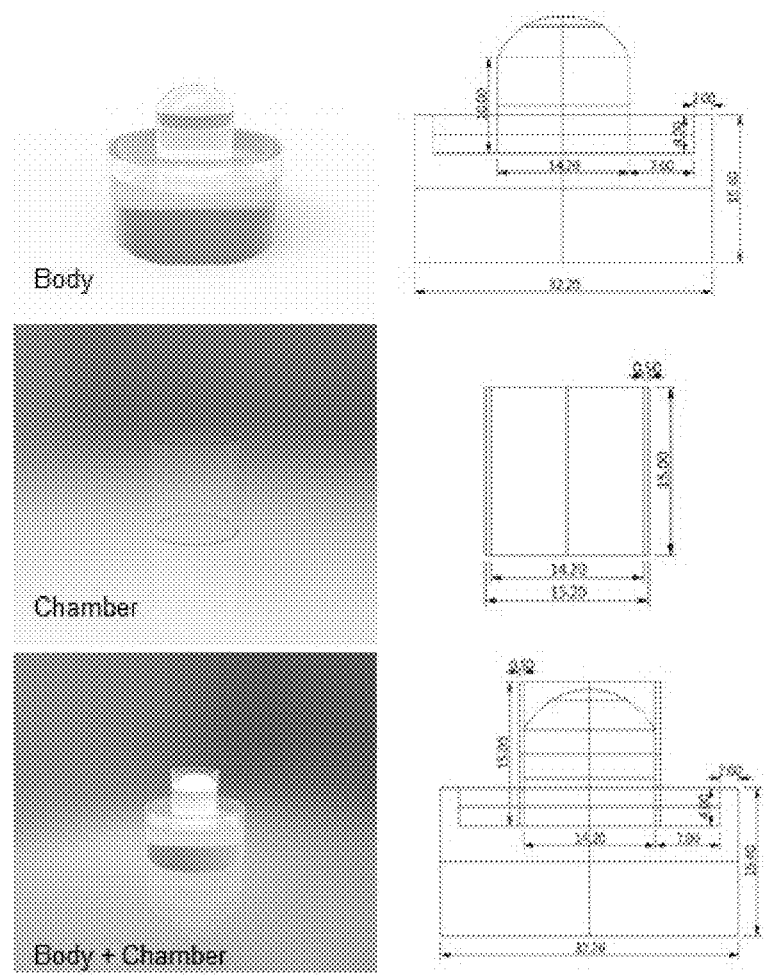

[Fig. 2]
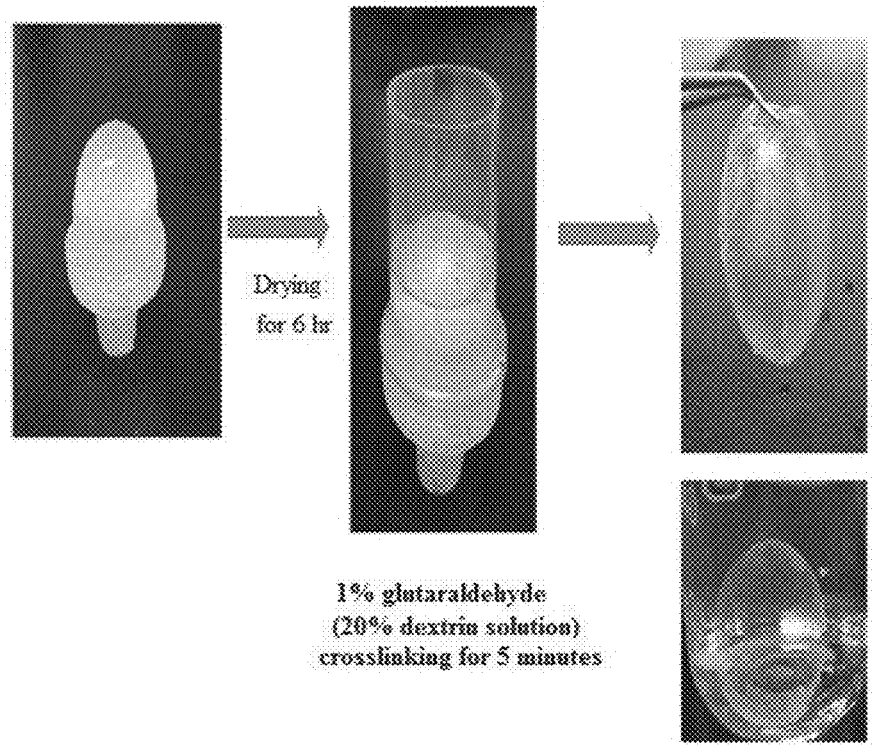
[Fig. 3]
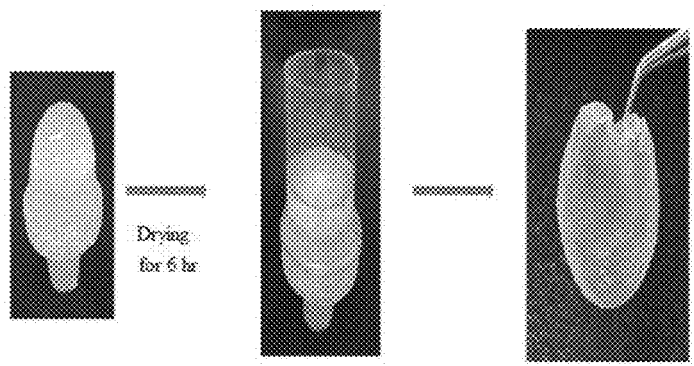

[Fig. 4]
Normal Amniotic Membrane
73.12 um
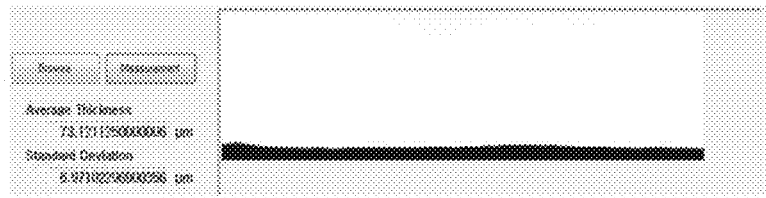
Glutaraldehyde Cross-linking Amniotic Membrane
36.36 um
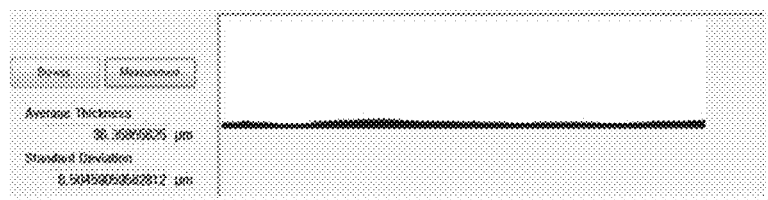
Dialdehyde Starch Cross-linking Amniotic Membrane
53.46 um
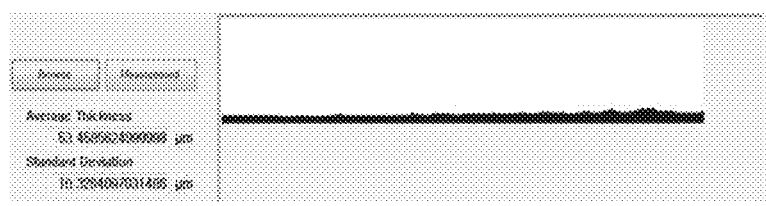

[Fig. 5]
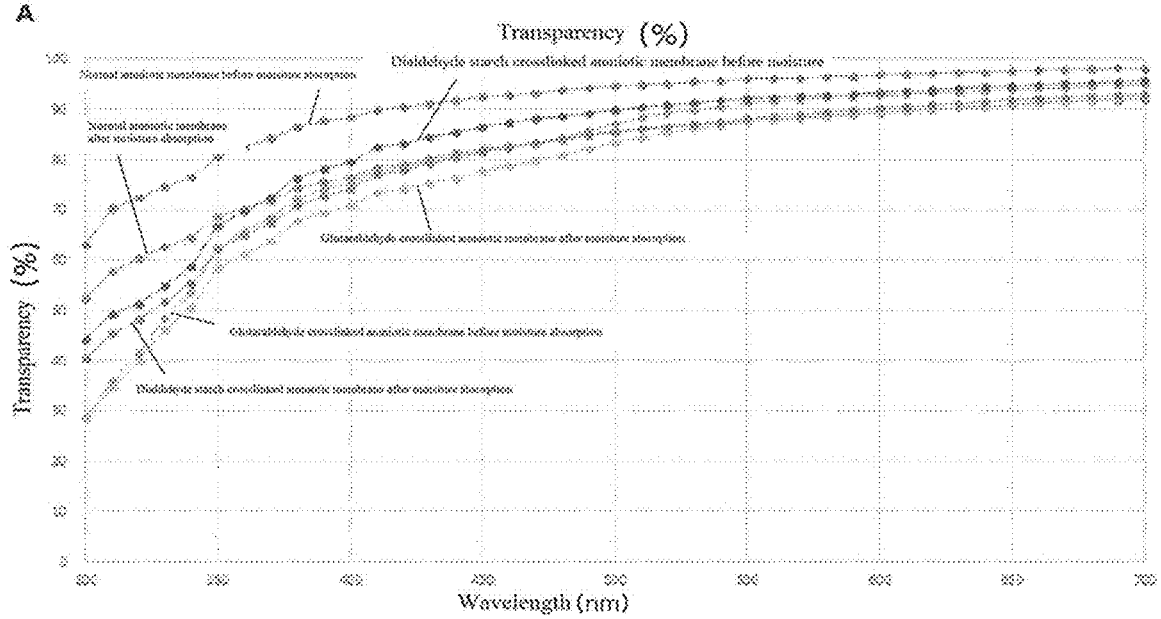
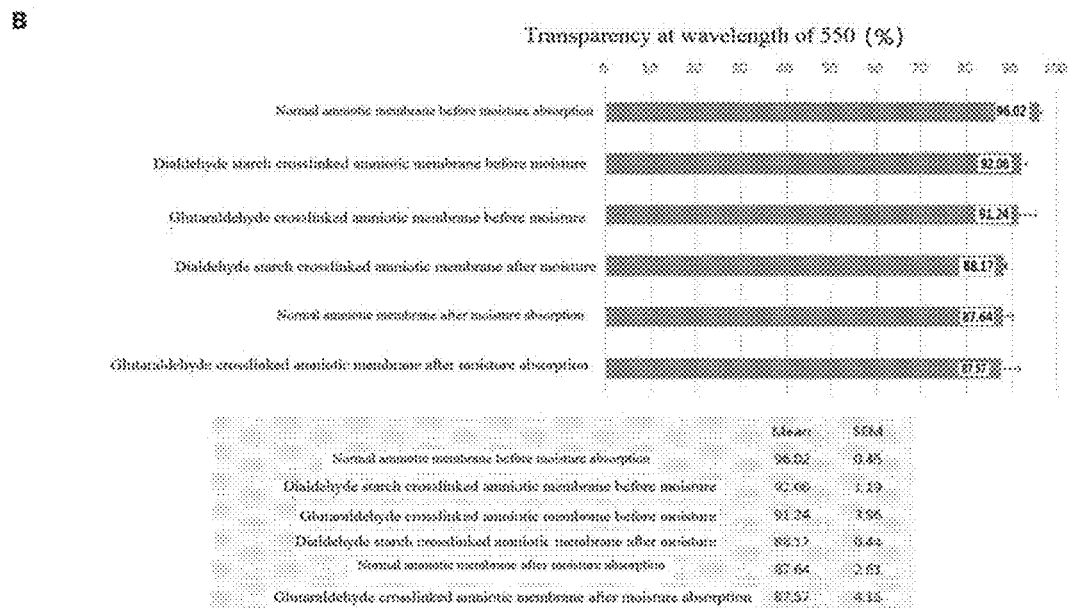

[Fig. 6]
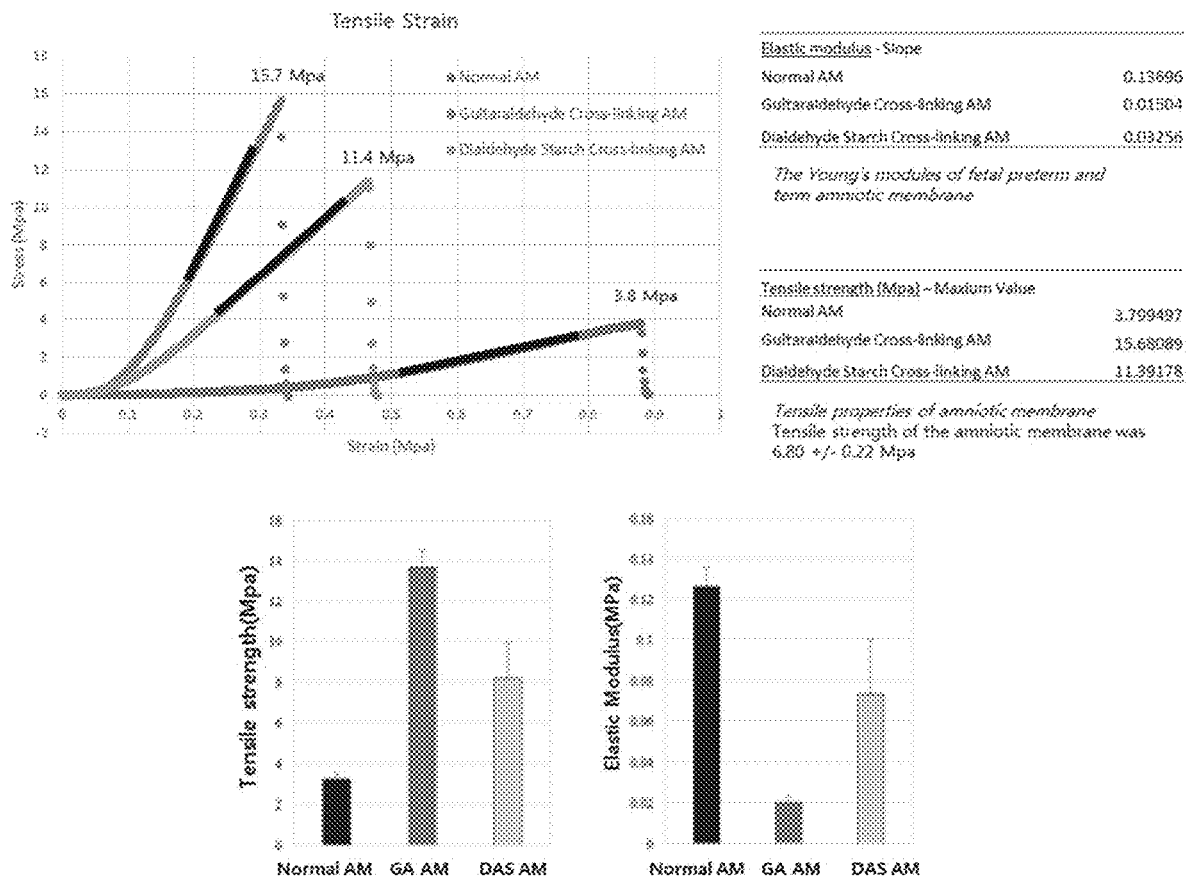

[Fig. 7]
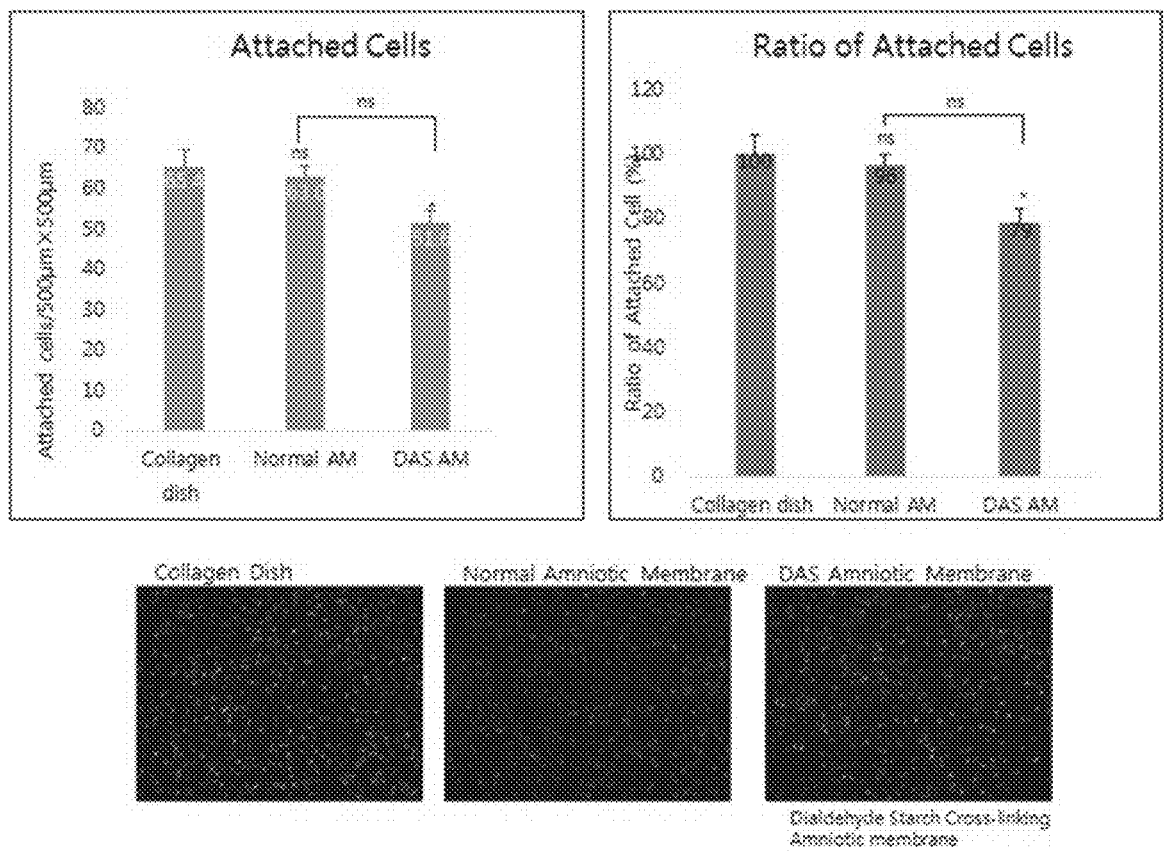

[Fig. 8]
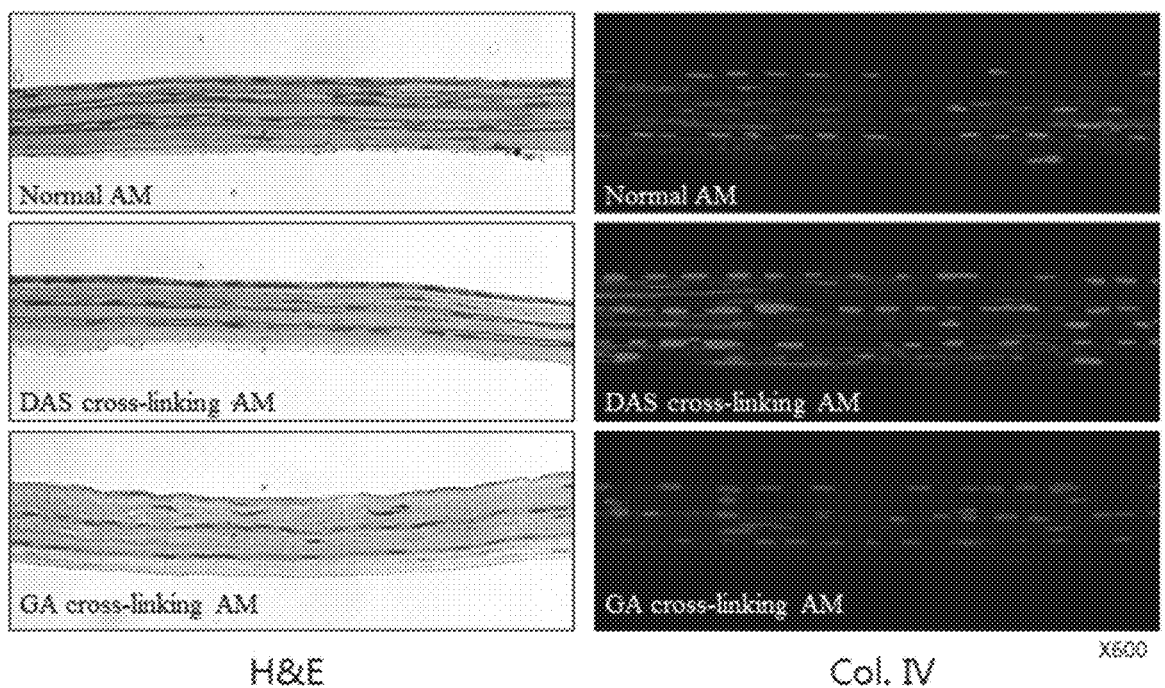

[Fig. 9]
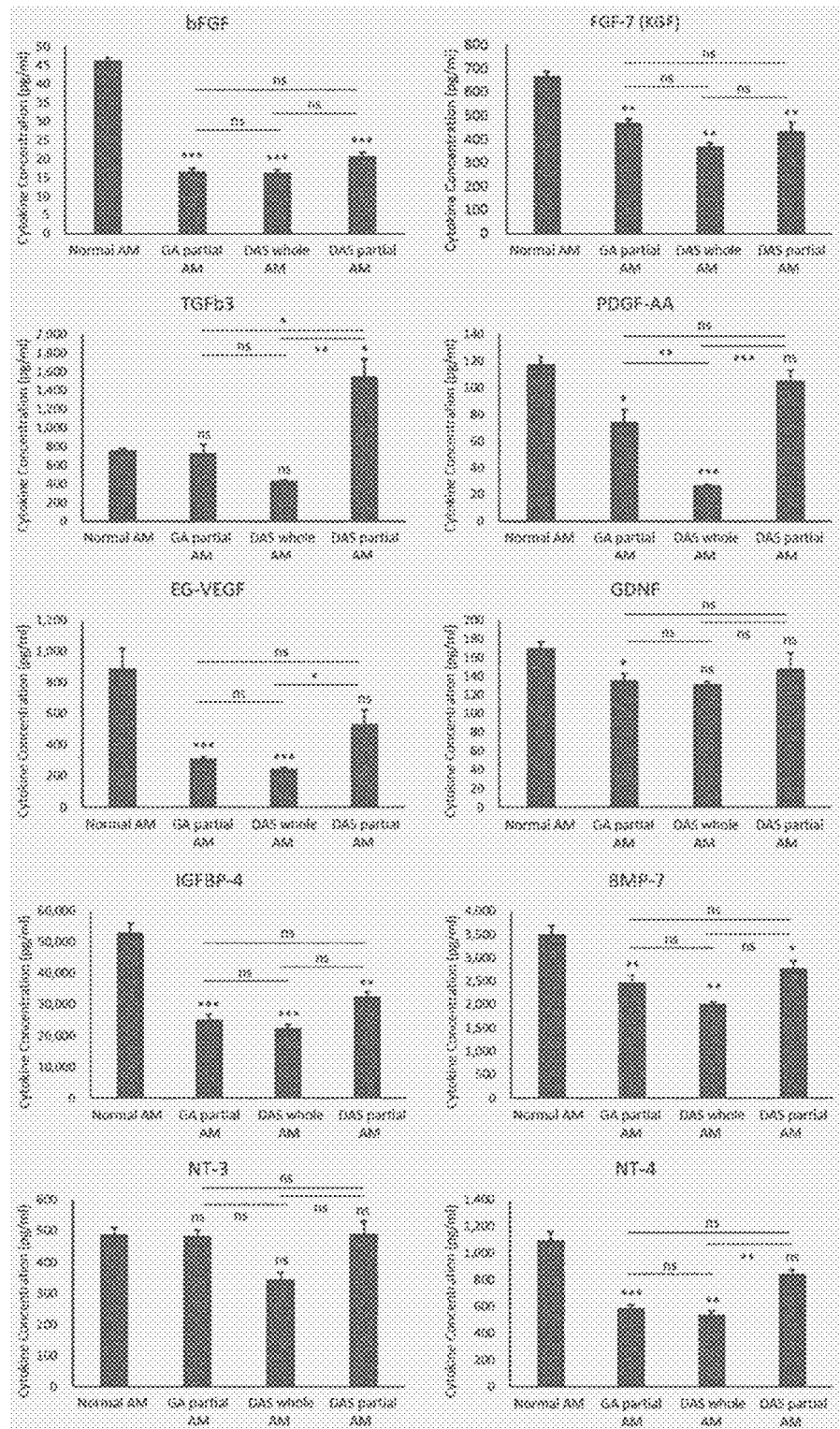

[Fig. 10]
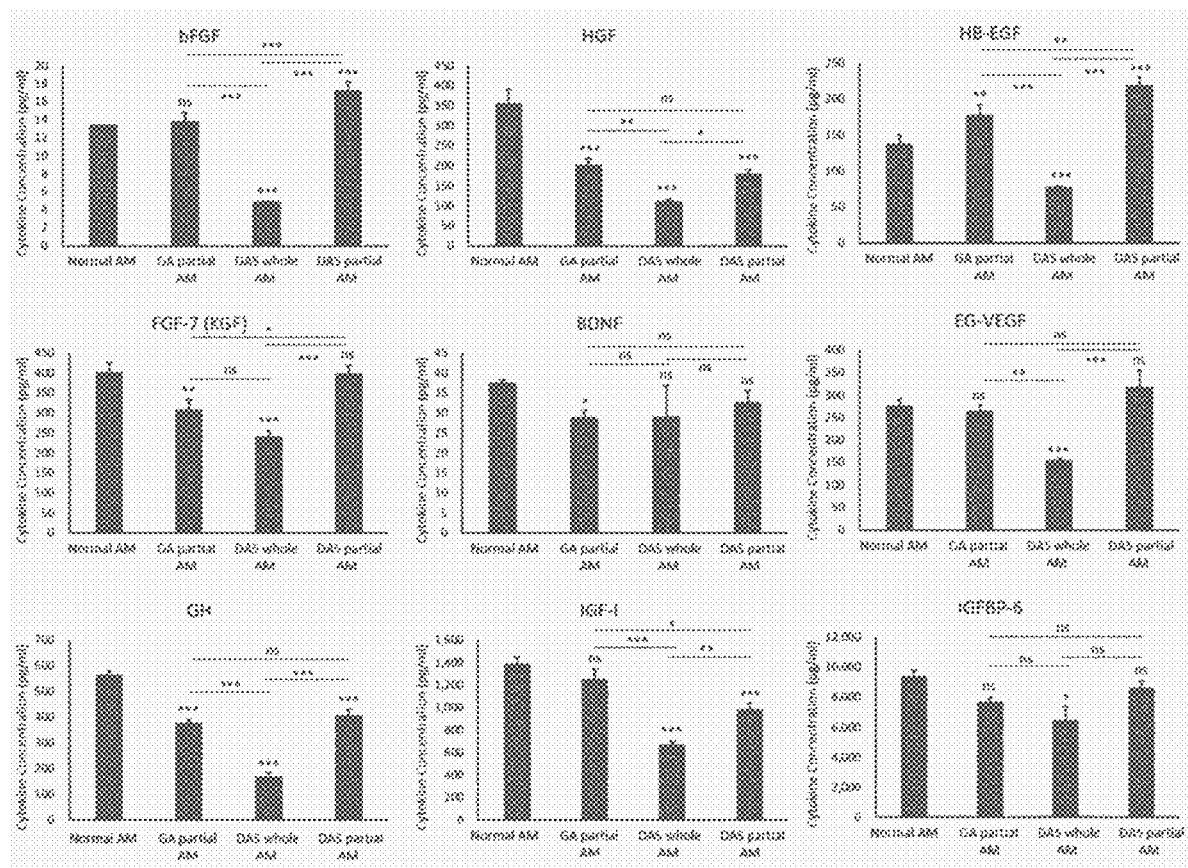

[Fig. 11]
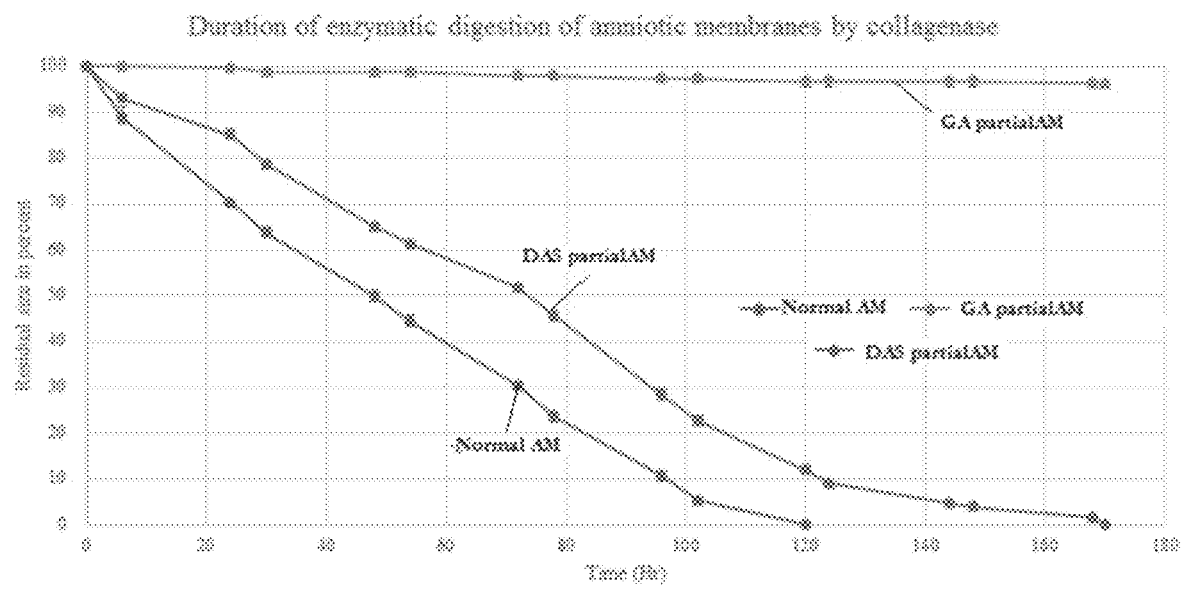
[Fig. 12]
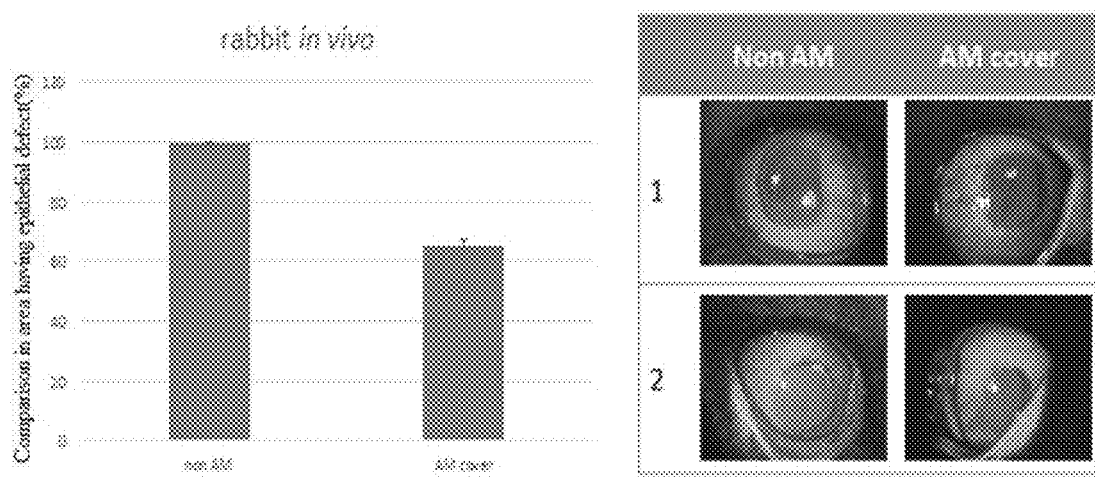

PARTIALLY CURED CONTACT LENS-TYPE AMNIOTIC MEMBRANE DRESSING AND METHOD OF MANUFACTURING SAME

TECHNICAL FIELD

The present disclosure relates to a contact lens-type amniotic membrane dressing manufactured using a partially cured amniotic membrane, and a method for manufacturing the same.

BACKGROUND ART

The amniotic membrane is the innermost membrane of the placenta that surrounds the fetus and acts as a barrier to protect the fetus from various infections and immune responses from the mother. The amniotic membrane is 0.2 to 0.5 mm thin and translucent, and is composed of simple cubic epithelium, thick basement membrane, and avascular mesenchymal stroma. Since the amniotic membrane does not have smooth muscle cells, nerves, lymphatic vessels, and blood vessels, it does not exhibit rejection after transplantation. Thus, the amniotic membrane is attracting attention recently. Further, since the role of amniotic membrane in promoting epithelialization and suppressing scar formation in the wound healing process has been known, efforts to implant the amniotic membrane in various ophthalmic diseases have been continued.

In order to implant the amniotic membrane itself into the cornea and conjunctiva, the technique of suturing using sutures has been attempted. However, the suture by surgery has a complicated process. Recently, attempts have been made to heal ocular wounds using amnion dressings.

The technologies that have been attempted recently include a lens type fixed with a plastic ring and a non-fixed moisture absorption disk (sheet) type. The lens-type product has convenience and fixability of the amniotic membrane for surgical procedure, but a peripheral portion of the product is made of hard plastic, such that the feeling of a foreign object in the eyeball after a procedure is high, causing the patient to feel discomfort. Further, the treatment effect is inferior because the product does not adhere to the cornea. The price thereof is also high, and thus there is a limitation that it may not be widely used in general corneal wound treatment. The disc (sheet) type product has price competitiveness and lowers the patient's rejection feeling, thereby to solve the problem of the conventional lens type product. However, the disc (sheet) type product is not fixed, and thus the disc (sheet) type product moves on a surface of the patient's eye. For this reason, the amniotic membrane fixed without sutures are currently rarely used. Although the number of patients with ocular surface diseases in the market is increasing due to environmental problems such as the increase of fine dust and the living environment that constantly encounters multimedia, there is a need for a new type of a contact lens-type dressing that may solve all the above problems and may be effectively used.

DISCLOSURE

Technical Purpose

The present inventor was researching to solve the problem of the conventional sheet type and lens-type ocular dressings using an amniotic membrane having wound healing effect, and thus recognized that a contact lens-type amniotic membrane dressing manufactured by partially curing a peripheral portion of the amniotic membrane has excellent biocompatibility, and excellent lens compatibility such as transparency and tensile strength, and excellent growth factor secretion ability and corneal wound regeneration effect. In this way, the present disclosure was completed.

Therefore, a purpose of the present disclosure is to provide a method for manufacturing a partially cured contact lens-type amniotic membrane dressing, and a partially cured contact lens-type amniotic membrane dressing manufactured by the method.

Technical Solution

In order to achieve the above purpose, the present disclosure provides a method for manufacturing a partially cured contact lens-type amniotic membrane dressing, the method including (1) a step of placing an amniotic membrane on a convex protrusion of a mold body that corresponds to a curvature of an eye, and then drying the amniotic membrane; (2) a step of combining a chamber with the mold body on which the amniotic membrane dried in the (1) step is placed; and (3) a step of filling the chamber with a crosslinking agent so that only a peripheral portion of the amniotic membrane is immersed in the crosslinking agent, and partially curing the peripheral portion of the dried amniotic membrane.

Further, the present disclosure provides a partially cured contact lens-type amniotic membrane dressing as manufactured by the method.

Advantageous Effects

The method for manufacturing the partially cured contact lens-type amniotic membrane dressing according to the present disclosure may be simple and may manufacture the contact lens-type amniotic membrane dressing without foreign substances. The partially cured contact lens-type amniotic membrane dressing as manufactured by the method has excellent biocompatibility, and excellent lens compatibility such as transparency and tensile strength, as well as excellent wound regeneration effect, compared to a fully cured contact lens-type amniotic membrane dressing, and thus may be usefully used in the treatment of the ocular diseases such as ocular corneal damage.

DESCRIPTION OF DRAWINGS

FIG. 1 is a diagram showing a configuration of a cast (mold) for manufacturing a partially cured contact lens dressing according to the present disclosure and is a diagram showing a body, a chamber and a combination thereof.

FIG. 2 is a diagram showing each of a process of manufacturing a contact lens-type amniotic membrane dressing using glutaraldehyde as a crosslinking agent and a contact lens-type amniotic membrane dressing manufactured via this process.

FIG. 3 is a diagram showing each of a process of manufacturing a contact lens-type amniotic membrane dressing using dialdehyde starch as a crosslinking agent and a contact lens-type amniotic membrane dressing manufactured via this process.

FIG. 4 is a diagram showing a thickness measurement result of each of partially cured contact lens-type amniotic membrane dressings as manufactured using an amniotic membrane without treatment with a crosslinking agent, and using an amniotic membrane with treatment with each of glutaraldehyde (GA) and dialdehyde starch (DAS) as the crosslinking agent.

FIG. 5 is a diagram showing measurement results of transparency before and after water-absorption of a contact lens-type amniotic membrane dressing. (a) in FIG. 5 shows results of measuring the transparency before and after the water-absorption of each of the partially cured contact lens-type amniotic membrane dressings manufactured using an amniotic membrane without treatment with a crosslinking agent, and using an amniotic membrane with treatment with each of glutaraldehyde (GA) and dialdehyde starch (DAS) as the crosslinking agent, at various wavelengths. (b) in FIG. 5 shows the result of measuring the transparency before and after the water-absorption of each of the partially cured contact lens-type amniotic membrane dressings manufactured using an amniotic membrane without treatment with a crosslinking agent, and using an amniotic membrane with treatment with each of glutaraldehyde (GA) and dialdehyde starch (DAS) as the crosslinking agent, at 550 nm wavelength.

FIG. 6 is a diagram showing the result of identifying a tensile strength of each of the partially cured contact lens-type amniotic membrane dressings manufactured using an amniotic membrane (normal AM) without treatment with a crosslinking agent, and using an amniotic membrane with treatment with each of glutaraldehyde (GA) and dialdehyde starch (DAS) as the crosslinking agent. X-axis: strain=time X speed/grip, Y-axis: stress=force (kg)/thickness ($m^2$). A slope of a linear section of the graph=elastic modulus. a in FIG. 6 is a graph showing the result of identifying the tensile strength according to treatment with the crosslinking agent. b in FIG. 6 is a diagram showing the elastic modulus and a tensile strength according to treatment with the crosslinking agent.

FIG. 7 is a diagram showing the results of identifying, based on cell adhesion, cytotoxicity to human corneal epithelial cells of the partially cured contact lens-type amniotic membrane dressings manufactured using an amniotic membrane (normal AM) without treatment with a crosslinking agent, and using an amniotic membrane with treatment with dialdehyde starch (DAS) as the crosslinking agent.

FIG. 8 is a diagram showing the results of histological analysis via staining of each of the partially cured contact lens-type amniotic membrane dressings manufactured using an amniotic membrane (normal AM) without treatment with a crosslinking agent, and using an amniotic membrane with treatment with each of glutaraldehyde (GA) and dialdehyde starch (DAS) as the crosslinking agent.

FIG. 9 shows comparisons between TFGb3, PDGF-AA, EG-VEGF, GDNF, IGFBP-4, BMP-7, NT-3, and NT-4 growth factor secretion capacity by the partially cured contact lens-type amniotic membrane dressings manufactured using an amniotic membrane fully crosslinked with dialdehyde starch (DAS), using an amniotic membrane (DAS partial AM) partially crosslinked with dialdehyde starch (DAS), and using an amniotic membrane (GA partial AM) partially crosslinked with glutaraldehyde (GA) as the crosslinking agent in a sample in a culture fluid form.

FIG. 10 shows comparisons between bFGF, HGF, HB-EGF, FGF-7, BDNF, EG-VEGF, GH, IGF-I, and IGFBP-6 growth factor secretion capacity by the partially cured contact lens-type amniotic membrane dressings manufactured using an amniotic membrane fully crosslinked with dialdehyde starch (DAS), using an amniotic membrane (DAS partial AM) partially crosslinked with dialdehyde starch (DAS), and using an amniotic membrane (GA partial AM) partially crosslinked with glutaraldehyde (GA) as the crosslinking agent in a sample in a powder form.

FIG. 11 is a diagram showing the results of identifying the resistance to collagenase degradation of the partially cured contact lens-type amniotic membrane dressing according to the present disclosure.

FIG. 12 shows a diagram showing the results of identifying corneal epithelium wound healing effect after each of the partially cured contact lens-type amniotic membrane (AM cover) dressing according to the present disclosure and a amniotic membrane dressing (non-AM) manufactured without treatment with a crosslinking agent is applied on a rabbit cornea with damaged corneal epithelium.

MODES OF THE INVENTION

The present disclosure provides a method for manufacturing a partially cured contact lens-type amniotic membrane dressing, the method including (1) a step of placing an amniotic membrane on a convex protrusion of a mold body that corresponds to a curvature of an eye, and then drying the amniotic membrane; (2) a step of combining a chamber with the mold body on which the amniotic membrane dried in the (1) step is placed; and (3) a step of filling the chamber with a crosslinking agent so that only a peripheral portion of the amniotic membrane is immersed in the crosslinking agent, and partially curing the peripheral portion of the dried amniotic membrane.

According to the method for manufacturing a partially cured contact lens-type amniotic membrane dressing according to the present disclosure, the contact lens-type amniotic membrane dressing may be manufactured without foreign substances via a simple method. The contact lens-type amniotic membrane dressing has excellent biocompatibility, and excellent lens compatibility such as transparency and tensile strength, and also excellent wound regeneration effect, compared to a fully cured contact lens-type amniotic membrane dressing.

Hereinafter, the present disclosure will be described in detail.

First, the method includes (1) a step of placing an amniotic membrane on a convex protrusion of a mold body that corresponds to a curvature of an eye, and then drying the amniotic membrane. This step includes preparing the amniotic membrane as a material for a contact lens dressing. In the present disclosure, the amniotic membrane may be a mammal-derived amniotic membrane. Preferably, it may be a human-derived amniotic membrane.

The amniotic membrane which may be used for the present disclosure may be obtained directly from the excised placenta. Specifically, the obtaining method may include washing the placenta, and then peeling the amniotic membrane little by little from the chorionic membrane, and then spreading the amniotic membrane such that the epithelium faces downwards and removing the chorionic membrane and cruor. A thus obtained amniotic membrane may be used for manufacturing a contact lens-type amniotic membrane dressing. All amniotic membranes which are usually classified based on a storage scheme may be used for manufacturing the contact lens-type amniotic membrane dressing according to the present disclosure. For example, a lyophilized amniotic membrane or a cryopreserved amniotic membrane may be used for manufacturing the contact lens-type amniotic membrane dressing according to the present disclosure. The amniotic membrane may then be sterilized using gamma rays.

The prepared amniotic membrane is placed on the protrusion of the mold body having a curvature corresponding to the curvature of the eye for manufacturing the partially cured contact lens-type amniotic membrane dressing. The mold may include the body on which the amniotic membrane is placed and dried, and the chamber that forms a space where the crosslinking agent and the amniotic membrane are crosslinked with each other.

The body and the chamber may be manufactured using 3D printing materials. Preferably, the body and the chamber may be manufactured using polydimethylsiloxane (PDMS) or polylactic acid (PLA). The body is manufactured to have a protrusion in a cylindrical shape. The body protrusion is manufactured to have the curvature corresponding to that of the lens. The curvature of the mold may be appropriately adjusted according to the purpose. For example, in order to manufacture an amniotic membrane suitable for Koreans, the curvature may be designed based on a radius of curvature of the eye of Koreans using reference books and statistics known in the art. The chamber of the mold has a hollow cylinder shape to receive the crosslinking agent. A size of the chamber may be adjusted so that the chamber may be combined with the body.

The amniotic membrane may be placed on the protrusion of the body and may be dried thereon. Preferably, the amniotic membrane is placed on the protrusion of the mold so that a face of the membrane on which the epithelial cells are present directly contact the mold, and then the moisture may be removed therefrom using a moisture adsorption paper and then the membrane may be dried naturally.

The amniotic membrane according to the present disclosure may be embodied as a single membrane, or as a stack of two or more amniotic membranes. In the latter case, drying of a first amniotic membrane is completed, and then a second amniotic membrane is placed on the first membrane and then dried. In this way, the contact lens-type amniotic membrane dressing composed of the stack of the plurality of amniotic membranes may be manufactured.

The (2) step according to the present disclosure includes combining the chamber with the body where the amniotic membrane dried in the (1) step is located.

When the body and the chamber are combined with each other, a distal end of the protrusion of the cylindrical shape of the body may have a higher vertical level than that of a top of the chamber or may be located at or above ½ of a vertical level of the top of the chamber. When the body and the chamber are combined with each other, a space in which a solution containing a crosslinking agent may be received is formed between the chamber and the body. The solution containing the crosslinking agent may be injected into the space, thereby to induce the binding of the amniotic membrane present on the body to the crosslinking agent.

The step (3) according to the present disclosure includes filling the chamber with the crosslinking agent so that only the peripheral portion of the amniotic membrane is immersed in the crosslinking agent and partially curing the peripheral portion of the dried amniotic membrane.

The crosslinking agent according to the present disclosure may include, without limitation, all known substances in the art that may induce crosslinking of the amniotic membrane. Examples thereof may include carbodiimide, EDC (or EDAC; 1-ethyl-3-(3-dimethylaminopropyl)carbodiimide), dialdehyde starch (DAS), glutaraldehyde, formaldehyde, hexamethylene diisocyanate (HMDI), dextran or glucose solution. Preferably, the crosslinking agent may be dialdehyde starch (DAS) or glutaraldehyde. Most preferably, the agent may be dialdehyde starch (DAS).

When using glutaraldehyde as a crosslinking agent, 0.05 to 0.3%, preferably 0.1% of glutaraldehyde may be used. The glutaraldehyde may be dissolved in a 20% dextran solution for use. Further, when dialdehyde starch is used as a crosslinking agent, dialdehyde starch having a concentration of 30 to 50 mg/ml, preferably 45 mg/ml may be used. The crosslinked amniotic membrane may be stored in a cryopreserved manner or a lyophilized manner. Sterile storage treatment using gamma rays may be further executed.

In accordance with the present disclosure, the partially cured contact lens-type amniotic membrane dressing means that only a portion of the contact lens-type amniotic membrane dressing is cured using the crosslinking agent. Preferably, the partially cured contact lens-type amniotic membrane dressing means that only the peripheral portion of the contact lens-type amniotic membrane dressing is cured. In the present disclosure, the "peripheral portion" of the contact lens-type amniotic membrane refers to an edge portion of the amniotic membrane excluding a center region of the amniotic membrane. Preferably, the peripheral portion may mean a portion between the amniotic membrane edge and a point of ⅓ of a distance from the amniotic membrane edge to the amniotic membrane center, and more preferably, a portion between the amniotic membrane edge and a point of ½ of a distance from the amniotic membrane edge to the amniotic membrane center. In order to manufacture the partially cured contact lens-type amniotic membrane dressing in which only the peripheral portion is partially crosslinked, the dried amniotic membrane located on the protrusion of the body may only partially contact the crosslinking agent present in the chamber during the manufacturing process. The chamber may be filled with the crosslinking agent so that only the peripheral portion of the amniotic membrane is immersed therein.

In accordance with the present disclosure, it is preferable that the partial curing in the (3) step is performed at room temperature, 2 to 10 minutes at room temperature, or preferably 5 minutes at room temperature.

The manufacturing method according to the present disclosure may further include a step (4) removing the crosslinking agent from the chamber and stabilizing the membrane for 0.5 to 2 minutes at room temperature by filling ½ of a volume of the chamber with NaBH$_4$/EtOH solution.

The (4) step includes removing the crosslinking agent from the chamber and stabilizing the partially cured amniotic membrane in which the partial crosslinking reaction has occurred. The amniotic membrane may be stabilized by adding NaBH$_4$/EtOH to the chamber in a volume similar to that of the crosslinking agent.

Further, the manufacturing method according to the present disclosure may further include a (5) step for obtaining the partially cured amniotic membrane and cutting the same into a contact lens shape.

The step of cutting the membrane into a contact lens shape may be performed using a conventional technique well known in the art. For example, this step may be carried out using a process such as rotational cutting using lathe or a laser.

Further, the manufacturing method according to the present disclosure may further include a (6) step for washing the amniotic membrane cut into the contact lens shape in the (5) step with glycine.

Detoxification is performed via the (6) step. The washing step may be particularly suitable for the manufacturing method using dialdehyde starch (DAS) as a crosslinking agent.

Glycine used in the washing process may be 0.1 to 0.3 M glycine PBS. Detoxification takes place via the washing step, such that the partially cured contact lens-type amniotic membrane dressing having superior biocompatibility may be obtained.

Further, in the manufacturing of the contact lens-type amniotic membrane dressing according to the present disclosure, the washed amniotic membrane dressing may be partially cured and then freeze-dried and then stored at room temperature or otherwise frozen, for example, at −90 to −50° C., preferably −80 to −70° C. Therefore, the manufacturing method according to the present disclosure may further include (7) step for lyophilizing or freezing the amniotic membrane as washed with glycine in the (6) step.

Thereafter, the manufactured contact lens-type amniotic membrane dressing may be sterilized using gamma rays.

Further, the present disclosure provides the partially cured contact lens-type amniotic membrane dressing as manufactured by the above method.

The contact lens-type amniotic membrane dressing according to the present disclosure is characterized in that only the peripheral portion of the amniotic membrane is partially cured. That is, the partially cured contact lens-type amniotic membrane dressing may be achieved. The peripheral portion of the amniotic membrane may be characterized in that the peripheral portion extends from the amniotic membrane edge to a point of at most ½ of the distance from the amniotic membrane edge to the amniotic membrane center.

The contact lens-type amniotic membrane dressing manufactured by crosslinking the peripheral portion as described above is finally cut such that the membrane is fixed in a ⅓ of a region from the amniotic membrane edge to the amniotic membrane center, and is not fixed in a remaining ⅔ thereof.

The partially cured contact lens-type amniotic membrane dressing according to the present disclosure is different from the fully cured contact lens-type amniotic membrane dressing in which only the peripheral portion of the contact lens-type amniotic membrane is cured, thereby achieving excellent physical properties including improved biocompatibility, tensile strength, transparency, and ability to secrete growth factors.

As long as all the characteristics of the partially cured contact lens-type amniotic membrane dressing according to the present disclosure in which only the peripheral portion of the amniotic membrane is partially cured is maintained, the method for manufacturing the dress is not particularly limited. However, preferably, the partially cured contact lens-type amniotic membrane dressing may be manufactured using the manufacturing method according to the present disclosure.

The partially cured contact lens-type amniotic membrane dressing may be characterized by having a high tensile strength of 2 to 4 times that of the amniotic membrane without the treatment with the crosslinking agent, and may be characterized in that the ability to secrete growth factors thereof is further increased compared to the fully cured contact lens-type amniotic membrane dressing.

The growth factor secretion ability may be compared in both the culture medium and powder states. The partially cured contact lens-type amniotic membrane dressing according to the present disclosure has superior growth factor secretion ability compared to the fully cured contact lens-type amniotic membrane dressing in both the states.

For example, the partially cured contact lens-type amniotic membrane dressing according to the present disclosure may exhibit similar or remarkably excellent secretion of growth factors including the TFGb3, PDGF-AA, EG-VEGF, GDNF, IGFBP-4, BMP-7, NT-3, and NT-4 (in the culture medium state), and bFGF, HGF, HB-EGF, FGF-7, BDNF, EG-VEGF, GH, IGF-I, IGFBP-6 (in the powder state), compared to the amniotic membrane fully crosslinked with dialdehyde starch. Particularly, the partially cured contact lens-type amniotic membrane dressing partially cured using dialdehyde starch may exhibit remarkably superior growth factor secretion ability compared to fully cured contact lens-type amniotic membrane as well as the partially cured contact lens-type amniotic membrane dressing partially cured with glutaraldehyde.

Further, the partially cured contact lens-type amniotic membrane dressing according to the present disclosure may be used for treating ocular diseases or for treating ocular wounds.

In accordance with the present disclosure, the ocular disease or ocular wound refers to the damaged ocular surface, persistent epithelial defect, persistent conjunctival ulcer, peripheral corneal ulcer, ischemic keratitis, inflammatory keratitis, neurotrophic keratitis, limbalitis, aniridia, bullous keratopathy, Stevens-Johnson syndrome, ocular scarring pemphigus, Sjogren's syndrome, pterygium or virtual pterygium, multiple endocrine insufficiency, lesion resection, conjunctival tumor resection, stem cell transplantation, conjunctival inflammation, acute inflammation, acute conditions of chemical and thermal burns, corneal stromal fusion disease, rheumatoid keratopathy, viral conjunctivitis or a disease, disease or condition characterized by bacterial ulcers.

In accordance with the present disclosure, the ocular diseases may include, for example, corneal edema, corneal opacity, scarring, surface inflammation, intraocular inflammation, corneal neovascular disorder or dry eye syndrome.

Hereinafter, Examples are intended only for describing the present disclosure in more detail. It will be apparent to those of ordinary skill in the art to which the present disclosure belongs that the scope of the present disclosure is not limited to these Examples and is based on the gist of the present disclosure.

EXAMPLES

Example 1. Preparation of Materials for Contact Lens-Type Amniotic Membrane Dressing 1.1 Preparation of Amniotic Membrane The placenta extracted by cesarean section of a pregnant woman without complications was stored in a sterilized container, stored in a refrigerator, treated within 24 hours, and stored in an isolated state. After passing the tissue compatibility evaluation, the placenta was transferred to an implantable freezer and was stored therein. The placenta was placed in a medical container and washed with physiological saline to remove cruor. An incision was made using medical scissors from the umbilical side, and the amniotic membrane was removed little by little by using forceps from the chorion. After the peeling away, the poor-quality amniotic membrane at the edge thereof was cut off and the remaining amniotic membrane portion was obtained. The separated amniotic membrane was spread on a stainless plate while the epithelium faces downward, and then rubbed with hand to remove the remaining chorionic membrane and cruor. Rinse was repeated 5 times using physiological saline.

A sample for bacteriological examination was obtained and cultured. First, the sample was put into the antibiotic solution (sterile Earle's balanced salt solution) (containing penicillin 50 ug/ml, streptomycin 50 ug/ml, netilmycin 100 ug/ml, amphotericin B 2.5 ug/ml). The amniotic membrane was spread on a stainless plate while the epithelium faces downwards, and then covered with NC paper (nitrocellulose paper with a pore size of 0.45 μg) to attach the amniotic membrane to the NC paper. After the attaching, the membrane was cut into 3×3 cm or 10×10 cm size and the cut piece was transferred to a container (nalgene bottle) containing a storage solution as a mixture of DMEM (Dulbecco Modified Eagle Medium) and glycerin at 1:1. Then, the solution was stored frozen at −70° C. After all the treatment procedures, a second sterilization process was additionally performed with 15 KGy radiation irradiation.

1.2 Mold Preparation and Manufacturing of Contact Lens-Type Amniotic Membrane Dressing A mold made to fit the curvature of the Korean eye was prepared. FIG. 1 shows the design and structure of the mold as used. As shown in FIG. 1, the mold includes a body and a chamber. The body and chamber were combined to each other and then used in the contact lens manufacturing. The body and chamber of the mold were made of polydimethylsiloxane (PDMS) or polylacetic acid (LA). The amniotic membrane was placed on the protrusion of the body of the mold and dried. After filling the chamber with a crosslinking agent to induce partial crosslinking, the body and the chamber were coupled to each other, thereby to induce partial crosslinking of the amniotic membrane. The amniotic membrane of Example 1.1 having epithelial cells was used. The amniotic membrane was placed on the protrusion of the body so that the surface of the amniotic membrane on which the epithelial cells were present was directly in contact with the mold, and the moisture was removed with a moisture absorption paper and the membrane was then naturally dried. When the first amniotic membrane was dried, a second amniotic membrane was placed on the first membrane again and dried naturally.

Glutaraldehyde (hereinafter, 'GA') and dialdehyde starch (hereinafter 'DAS') were used as the crosslinking agent. The crosslinking agent was filled into the chamber so that only the peripheral portion of the amniotic membrane was immersed therein. The peripheral portion of the amniotic membrane was fixed while a region thereof from the amniotic membrane edge to up to a point of ⅓ (or ½ by diffusion) of the distance from the amniotic membrane edge to the center of the amniotic membrane was immersed. That is, a region of the amniotic membrane from the amniotic membrane edge to up to a point of ⅓ or ½ of the distance from the amniotic membrane edge to the center of the amniotic membrane was immersed.

More specifically, DAS (BOC sciences, New York, USA) was dissolved in PBS (phosphate-buffered saline) to reach 45 mg/ml, and the pH thereof was adjusted to 7.4. Fully melted DAS solution was filled into the chamber as much as ½ of the volume of the dried amniotic membrane. Then, the chamber was combined with the body of the mold on which the amniotic membrane was mounted, and then the membrane was crosslinked at room temperature for 5 minutes.

0.1% GA (=10 mM) (Merck, Darmstadt, Germany) was dissolved in a 20% solution of dextran. The GA dissolved solution was filled into the chamber as much as ½ of the volume of the amniotic membrane dried on the mold. The chamber was combined with the body of the mold on which the amniotic membrane was mounted, and the membrane was crosslinked at room temperature for 5 minutes.

The solution containing the crosslinking agent was removed from the chamber, and a 1% $NaBH_4$/EtOH solution was filled into the chamber by ½ of a volume of the chamber, and then reaction occurred at room temperature for 1 minute. The crosslinked amniotic membrane was cut into a contact lens shape with a diameter of 18 to 22 mm. The crosslinked amniotic membrane piece as cut into the contact lens shape was washed several times with 0.2 M glycine PBS. When cutting the membrane into the contact lens shape as the final product, a region of the product between the membrane edge and a point of ⅓ of the distance from the edge to the center of the contact lens-type amniotic membrane dressing was crosslinked and fixed. A remaining region of the product between the point of ⅔ of the distance from the edge to the center of the contact lens-type amniotic membrane dressing and the center thereof was cut and was not fixed. The prepared amniotic membrane was subjected to cryopreserve at −80° C. in a preservative solution in which glycerol and DMEM (dulcecco's modified eagle medium, phenol red free) were mixed with each other at 1:1. Further, the prepared amniotic membrane was subjected to lyophilizing and then storage at room temperature. The manufactured GA and DAS-treated partially cured contact lens-type amniotic membrane dressing is shown in FIG. 2 and FIG. 3.

Example 2

An experiment was performed to identify the physical properties of the contact lens-type amniotic membrane dressing manufactured in Example 1.

2.1 Measurement of Thickness and Transparency of Amniotic Membrane

A thickness of the amniotic membrane was measured at Pohang University of Science and Technology. The amniotic membrane was placed on the slide glass and photographed on a side thereof using Smart Drop (Femtobiomed, Korea) equipment, and then a thickness of the amniotic membrane was calculated in terms of length per pixel. As a comparative control, a normal amniotic membrane without the treatment with the crosslinking agent was used. As experimental groups, amniotic membranes crosslinked with GA and DAS were used. The results of measuring the thickness are shown in FIG. 4.

As shown in FIG. 4, the thickness of the amniotic membrane without the treatment with the crosslinking agent was 73.12 um. The thicknesses of the partially cured amniotic membranes with GA and DAS treatment were 36.36 um and 53.46 um, respectively. This result means that the thickness is reduced due to the partial crosslinking treatment with the crosslinking agent.

After measuring the absorbance of the amniotic membrane, transparency was calculated using an equation: absorbance=−log (transmittance (%))/100. The crosslinked amniotic membrane and the non-crosslinked amniotic membrane were cut to correspond to a size of a 96 well plate with a biopsy punch. After sufficiently removing moisture, absorbance was measured by reading the wavelength of 300 nm to 700 nm (on a 10 nm basis) using a microplate reader (Biotek, Winooski, USA). The transparency of the amniotic membrane was measured by converting the absorbance to the transparency using the above equation. In particular, the transparency at 550 nm wavelength was compared and analyzed. The result of measuring the transparency is shown in FIG. 5.

As shown in FIG. 5, the amniotic membrane without the treatment with the crosslinking agent and the amniotic membrane with the treatment with the crosslinking agent DAS before the water absorption had the highest transparency, but had no statistical significance. These results indicate that the transparency is not affected by the partially curing under DAS and GA treatment.

2.2 Tensile Strength Measurement

The measurement of the tensile strength of the amniotic membrane was carried out with the help of the laboratory of Pohang University of Science and Technology. After cutting the amniotic membrane into a size of 5 mm×15 mm, the both ends thereof were fixed with clips, and then pulled in both opposing directions with a constant force using a test equipment for measuring tensile strength (resolution: 0.1 N). A temporal value from a time point when pulling the membrane to the moment the amniotic membrane broke was measured and then was converted to a force per hour. The results are shown in FIG. 6.

As shown in FIG. 6, the mechanical properties varied according to the type of the crosslinking agent. It was identified that the partially cured amniotic membrane under GA treatment and the partially cured amniotic membrane under DAS treatment had increased modulus of elasticity and tensile strength than those of the normal amniotic membrane without the treatment with the crosslinking agent. The partially cured amniotic membrane treated with GA had tensile strength increased by about 4 times. The partially cured amniotic membrane treated with DAS had the tensile strength increased by about 3 times. These results show that the partially cured amniotic membrane that has undergone the crosslinking process had significantly increased physical strength, compared to the untreated normal amniotic membrane.

2.3 Cell Viability Measurement

In order to be worn on the cornea a contact lens, the membrane should not be toxic to the human cornea. Thus, cell viability was identified using human cornea epithelial cells (HCEC) which were first cultured in human cornea. First, the amniotic membrane was placed on a dish coated with collagen type 1 and slightly dried to adhere well thereto, and then HCEC was dispensed into the dish and was incubated for 48 hours in a 37° C. and 5% $CO_2$ incubator. Cell viability was identified using Live and Dead cell Assay (Abcam, Cambridge, UK). Cells in a 500 um×500 um region were counted repeatedly 5 times and then attached to the amniotic membrane to investigate a percentage of living cells thereon. The results are shown in FIG. 7.

As shown in FIG. 7, it was identified that the partially cured amniotic membrane with the DAS treatment exhibited no statistical difference in terms of the number and ratio of adherent cells, compared to the untreated normal amniotic membrane, and thus the biocompatibility thereof was very good.

2.4 Histological Analysis

Since one amniotic membrane was too thin to analyze, three amniotic membranes were stacked one on top of another and the stack was fixed and immersed in Tissue-Tek OCT compound (Sakura Finetek Europe, Zoeterwoudem, NL). The specimen was cut into 7 um thickness section, and the section was placed on SuperFrost Plus Microscope slides (Fisher Scientific), dried at room temperature for 30 minutes, and fixed to the slide for 5 minutes with 95% EtOH. After hematoxylin-eosin staining thereof, the membrane section was observed using an optical microscope. Collagen type IV as a protein constituting a basement membrane was identified via immunostaining. The tissue attached to the slide was washed with PBS and reaction thereof had occurred for 1 hour in a blocking solution containing 1% BSA to suppress non-specific reactions. A primary antibody was anti-collagen IV type (1:200, Abcam, Cambridge, UK), and was reacted with the membrane at 4° C. overnight. After washing away the primary antibody, Alexa-488-conjugated anti-rabbit (1:200, Abcam, Cambridge, UK) was used as secondary antibodies which reacted with the membrane at room temperature for 1 hour. Nuclear staining was counterstained using DAPI (4',6-diamidino-2-phenylindol). The results are shown in FIG. 8.

It was identified as shown in FIG. 8 that the cytoplasm indicated in pink color was not decreased and the collagen type IV was not reduced in the amniotic membrane partially cured with DAS or GA, compared to the untreated normal amniotic membrane. In particular, in the partially cured amniotic membrane with treatment with DAS, the cells and collagen type IV were clearly maintained.

2.5 Growth Factor Analysis

The amniotic membrane partially crosslinked according to the method of the present disclosure, and the untreated amniotic membrane were freeze-dried to obtain powders, respectively. A culture solution was obtained by applying the amniotic membrane to a cell culture dish and culturing the membrane in a medium containing no serum for more than 24 hours. After measuring a protein content of the powdery sample and the culture medium, growth factors included in each sample were analyzed. Human Growth Factor Array Q1 (Raybiotech, Norcross, GA, USA) was used. A standard curve was created using an analysis tool provided by Raybiotech and a concentration was measured.

For comparison with the fully cured contact lens-type amniotic membrane, the fully cured contact lens-type amniotic membrane was manufactured using DAS as a crosslinking agent and the expression of growth factors thereof was compared with that of the partially cured contact lens-type amniotic membrane. The fully cured contact lens-type amniotic membrane is manufactured in the same way as in Example 1. However, the method for producing the fully cured contact lens-type amniotic membrane included filling the chamber with DAS in a volume equal to the volume of the dried amniotic membrane and combining the chamber with the body of the mold on which the amniotic membrane was placed. The fully cured amniotic membrane was in contact with the DAS such that crosslinking occurred at room temperature for 5 minutes.

The amount of secretion of various growth factors was measured, and the results measured in the culture medium state are shown in FIG. 9, and the results measured in the freeze-dried powder state are shown in FIG. 10.

As shown in FIG. 9, the partially cured amniotic membrane (DAS partial AM) with DAS treatment and the partially cured amniotic membrane (GA partial AM) with GA treatment were compared with the fully cured AM with DAS treatment. The partially cured amniotic membrane (DAS partial AM) with DAS treatment and the partially cured amniotic membrane (GA partial AM) with GA treatment exhibited similar or remarkably superior TFGb3, PDGF-AA, EG-VEGF, GDNF, IGFBP-4, BMP-7, NT-3, NT-4 growth factor secretion ability compared to the fully cured AM with DAS treatment.

Further, as shown in FIG. 10, results of the comparative experiment about the secretion ability of the growth factor in the lyophilized powder state were similar to those in the culture medium state. The partially cured amniotic membrane (DAS partial AM) with DAS treatment and the partially cured amniotic membrane (GA partial AM) with GA treatment exhibited similar or remarkably superior bFGF, HGF, HB-EGF, FGF-7, BDNF, EG-VEGF, GH, IGF-I, IGFBP-6 growth factor secretion ability compared to the fully cured AM with DAS treatment.

These results indicate that the partially cured amniotic membrane has superior growth factor secretion ability compared to the fully cured amniotic membrane.

2.6 Collagenase Assay

When the amniotic membrane is resistant to collagenase as the main component that decomposes on the ocular surface, the membrane does not degrade on the ocular surface and may stay for a long time. Therefore, a collagenase assay was performed to identify whether the partially cured amniotic membrane according to the present disclosure has degradation resistance to treatment with collagenase. Specifically, the partially cured amniotic membrane (DAS partial AM) with DAS treatment and the partially cured amniotic membrane (GA partial AM) with GA treatment as obtained in the Example 1, and a normal amniotic membrane as control were cut into 1×1 cm pieces. Each piece was immersed in a petri dish containing 0.1% collagenase solution (EC 3.4.24.3, *Clostridium histolyticum*; Roche, Mannheim, Germany) in PBS at pH 7.5 and then observed at room temperature. A graph paper was attached to a bottom of the Petri dish, and a grid of the remaining amniotic membrane was counted. The calculated value is calculated as a percentage and the results are shown in FIG. 11.

As shown in FIG. 11, it was identified that the partially cured amniotic membrane has increased resistance to degrading enzymes compared to the normal amniotic membrane and may be maintained on the ocular surface for a relatively long time. This may prolong the damage recovery period by delaying, by about 2 to 3 days, the characteristics of the amniotic membrane in which the membrane naturally degrades and disappears from the eyeball surface. Further, it was identified that the partially cured amniotic membrane with GA treatment has greater resistance than that of the partially cured amniotic membrane with DAS treatment.

2.7 Enhancement of Epithelial Recovery by Partially Cured Contact Lens-Type Amniotic Membrane Animal experiments were performed using white rabbits. All experimental animals were adapted to the breeding environment before the experiment. After removing the entire corneal epithelial cells of the rabbit eye with a surgical knife, the partially cured amniotic membrane with DAS treatment according to Example of the present disclosure was worn on the rabbit cornea in a contact lens wearing manner and observed for 24 hours. After staining with sodium fluorescein, the epithelial recovery was observed via photographing with a slit lamp. The area without epithelial recovery was calculated using the ImageJ program. FIG. 12 shows the results of the comparison in the area having epithelial defects in rabbit cornea and the corresponding corneal epithelial damage recovery effect.

As shown in FIG. 12, it was identified that in the cornea of rabbits wearing the partially cured amniotic membrane with the DAS treatment in the contact lens manner, the epithelial damage area decreased by 62% compared to the unworn cornea on a first day after the wearing. This is a result showing that when the partially cured amniotic membrane is worn in a contact lens wearing manner, the recovery of the corneal epithelium may be promoted.

The contact lens-type amniotic membrane dressing manufactured by partially curing the amniotic membrane using the crosslinking agent as described above has excellent product competitiveness due to excellent transparency and tensile strength, and has excellent biocompatibility compared to the fully cured amniotic membrane, and has excellent secretion ability of growth factors such that the corneal epithelium may be effectively regenerated. Thus, the partially cured contact lens-type amniotic membrane dressing may be usefully used for the treatment of various eye diseases, particularly corneal injuries.

What is claimed is:

1. A partially cured contact lens-type amniotic membrane dressing characterized in that a peripheral portion of the amniotic membrane is all cured such that the whole contact lens-type amniotic membrane is partially cured wherein the peripheral portion of the amniotic membrane extends from an edge of the amniotic membrane to a point of ½ of a distance from the edge to a center of the amniotic membrane, wherein the partially cured contact lens-type amniotic membrane dressing has increased growth factor secretion ability compared to a fully cured contact lens-type amniotic membrane dressing.

2. The partially cured contact lens-type amniotic membrane dressing of claim 1, wherein the partially cured contact lens-type amniotic membrane dressing has a tensile strength greater by 2 to 4 times than a tensile strength of an amniotic membrane without treatment with a crosslinking agent.

3. The partially cured contact lens-type amniotic membrane dressing of claim 1, wherein the partially cured contact lens-type amniotic membrane dressing is used for treatment of ocular diseases.

4. The partially cured contact lens-type amniotic membrane dressing of claim 1, wherein the partially cured contact lens-type amniotic membrane dressing is used for treating ocular wounds.

* * * * *